United States Patent [19]

Herrold

[11] 4,372,944

[45] Feb. 8, 1983

[54] COSMETIC CREAM FORMULATION

[75] Inventor: Anne M. Herrold, Brownsburg, Ind.

[73] Assignee: Eli Lilly and Company, Indianapolis, Ind.

[21] Appl. No.: 289,653

[22] Filed: Aug. 3, 1981

[51] Int. Cl.³ .................... A61K 31/745; A61K 47/00
[52] U.S. Cl. ...................................... 424/83; 424/168; 424/358; 424/365
[58] Field of Search .................. 424/358, 365, 83, 363

[56] References Cited

U.S. PATENT DOCUMENTS 3,924,004 12/1975 Chang .................................. 424/358
4,268,526 5/1981 Vargas et al. ........................ 424/358
4,272,544 6/1981 Cella et al. ........................... 424/273

OTHER PUBLICATIONS

Harry, The Principles and Practice of Modern Cosmetics, vol. II, 1963, pp. 16 and 17.
Harry, The Principles and Practice of Modern Cosmetics, vol. I, 1963, pp. 140 to 144.
Ash, A Formulary of Cosmetics Preparations, 1977, pp. 255 to 259.

*Primary Examiner*—Dale R. Ore
*Attorney, Agent, or Firm*—Karen B. O'Connor; Arthur R. Whale

[57] ABSTRACT

A novel cosmetic skin cream formulation is described which is non-irritating and non-stinging.

1 Claim, No Drawings

COSMETIC CREAM FORMULATION

This invention relates to a novel cosmetic cream formulation, which is non-irritating and non-stinging.

It is, therefore, an object of the present invention to provide a sensitive cosmetic cream formulation. The cream can be used in conjunction with other cosmetic formulations.

The cream formulation is one of a four-component regime, which is used to treat sensitive skin. The other three components are: a cleanser, a toner, and a moisturizer. Each of the other three components is a separate invention; the cleanser is claimed in application Ser. No. 289,657, filed Aug. 3, 1981, the toner is claimed in application Ser. No. 289,656, filed Aug. 3, 1981, and the moisturizer is claimed in application Ser. No. 289,655, filed Aug. 3, 1981. The method of treating sensitive skin using the regime is claimed in application Ser. No. 289,658, filed Aug. 3, 1981. In addition, a cream pack formulation is claimed in application Ser. No. 289,654, filed Aug. 3, 1981.

The cream formulation consists essentially of, in percent by weight:

| Ingredients | Percent |
| --- | --- |
| white beeswax | 2.00 |
| distilled lanolin alcohols | 0.50 |
| white petrolatum | 2.00 |
| triglyceryl diisostearate | 5.50 |
| squalane (2,6,10,15,19,23-hexamethyl-tetracosane) | 5.00 |
| light mineral oil | 6.00 |
| isopropyl myristate | 5.00 |
| polyethylene homopolymer (1500 m. wt., density 0.91 g/cc) | 3.00 |
| polydimethylcyclosiloxane | 3.00 |
| quaternary bentonite (Bentone. No. 38) | 0.40 |
| 70% sorbitol solution | 5.00 |
| glyoxyldiureide | 0.50 |
| preservative | q.s. |
| deionized water | q.s. to 100% |

One skilled in the cosmetic formulation art will appreciate that various preservatives can be added to the formulation in sufficient quantities. These preservatives include the esters of p-hydroxybenzoic acid, such as methyl p-hydroxybenzoate, and propyl p-hydroxybenzoate; cis-1-(3-chloroallyl)-3,5,7-triaza-1-azoniaadamantane chloride; ethylenediaminetetraacetic acid (EDTA) and salts of EDTA; imidazolidinyl urea; sodium N-lauryl-β-iminodipropionate; and the like or any combination thereof. The total amount of preservative used can vary, but usually it is from about 0.3 to about 1.0 percent.

In addition, color and essence can be included in the formulation as desired. Color additives would include both natural and artificial dyes, such as carotenoid derivatives, D+C or F,D+C colors, iron oxides, and the like, while essences can include any non-irritating natural and artificial oils, perfumes, and the like.

The formulation is both non-irritating and non-stinging, according to standard cosmetic testing procedures. The first procedure utilized was the Lanman-Maibach Cumulative Irritation Test, which is a 21-day patch irritation procedure as described by Dr. B. M. Lanman at the Joint Conference on Cosmetic Sciences, Apr. 21-23, 1968 in Washington D.C. as further modified in Phillips, L., Steinberg M., Maibach, H., and Akers, W., *Toxicology and Applied Pharmacology* 21, 369-382 (1972). The non-stinging properties of the formulation were established by the Lactic Acid Sting Test as described in P. J. Frosch and A. M. Kligman: "A Method for Appraising the Stinging Capacity of Topically Applied Substances" *Journal of the Society of Cosmetic Chemists* 28, 197-209, May 1977.

In general, the individual ingredients used in the formulation should be of a quality or purity (such as U.S.P. or N.F.) suitable for cosmetic use.

The formulation is prepared by mixing the ingredients according to conventional methods and the preparation of this formulation is described in the following example. The example is illustrative of the formulation, but is not to be construed as limiting the invention.

EXAMPLE

Cream

Formulation:

| Phase | Ingredient | Percent by weight |
| --- | --- | --- |
| A | light mineral oil | 6.00 |
|   | Polyethylene 617 (Allied Chemical, polyethylene homopolymer, 1500 m. wt., density 0.91 g/cc, softening pt. 102° C., viscosity at 140° C. 145 cps) | 3.00 |
| B | white beeswax | 2.00 |
|   | Super Hartolan (Croda, distilled lanolin alcohols) | 0.50 |
|   | white petrolatum | 2.00 |
|   | Robane (Robeco, squalane) | 5.00 |
|   | Silicone Fluid 344 (Dow Corning, polydimethylcyclosiloxane) | 3.00 |
|   | triglyceryl diisostearate | 5.50 |
|   | isopropyl myristate | 5.00 |
|   | propylparaben (propyl p-hydroxybenzoate) | 0.10 |
| C | Bentone No. 38 (NL Industries, quaternary bentonite) | 0.40 |
| D | deionized water | 60.38 |
|   | 70% sorbitol solution | 5.00 |
|   | imidazolidinyl urea | 0.30 |
|   | Allantoin (Sutton and Schuylkill, glyoxyldiureide) | 0.50 |
|   | methylparaben (methyl p-hydroxybenzoate) | 0.20 |
| E | deionized water | 1.00 |
|   | Dowicil 200 (Dow Chemical, cis-1-(3-chloroallyl)-3,5,7-triaza-1-azoniaadamantane chloride) | 0.10 |
| F | Annatto, O.S. (natural orange dye, which is a carotenoid derivative dispersed in corn oil mono-glycerides of the fatty acids derived from vegetable oil; CI 75120) | 0.02 |

Procedure:

All the ingredients of Phase A are combined and heated to about 90°-95° C. in a jacketed tank equipped with a propeller stirrer. Phase A is stirred rigorously until all of the Polyethylene 617 is dissolved and should be crystal clear with no undissolved particles. In a separate jacketed tank equipped with a propeller mixer, the ingredients of Phase B are melted together and heated to about 90°-95° C., making sure that all of the propylparaben is dissolved.

Next, Phase C is carefully sprinkled in Phase B and Phase BC is stirred vigorously to disperse the Bentone No. 38. Phase A is added to Phase BC, mixed, and maintained at about 90°-95° C.

In a jacketed tank equipped with a homomixer and sweep stirrer, the Phase D ingredients are dissolved in the deionized water of Phase D and then heated to 90°–95° C., making sure that all of the methylparaben is dissolved. Phase ABC is added to Phase D and mixed with the homomixer and sweep stirrer for about 15 minutes at about 90°–95° C. The product will become very viscous.

Mixing with the sidesweep and homomixer is continued and the product is cooled to about 40°–45° C. The Dowicil 200 is dissolved in the deionized water of Phase E and then Phase E is added to Phase ABCD.

Phase F is added and mixing is continued with the sidesweep only. The product is then cooled to about 30°–35° C.

I claim:

1. A cosmetic cream formulation consisting essentially of, in percent by weight:

| Ingredients | Percent |
| --- | --- |
| white beeswax | 2.00 |
| distilled lanolin alcohols | 0.50 |
| white petrolatum | 2.00 |
| triglyceryl diisostearate | 5.50 |
| squalane (2,6,10,15,19,23-hexamethyltetracosane) | 5.00 |
| light mineral oil | 6.00 |
| isopropyl myristate | 5.00 |
| polyethylene homopolymer (1500 m. wt., density 0.91 g/cc) | 3.00 |
| polydimethylcyclosiloxane | 3.00 |
| quaternary bentonite (Bentone. No. 38) | 0.40 |
| 70% sorbitol solution | 5.00 |
| glyoxyldiureide | 0.50 |
| preservative | q.s. |
| deionized water | q.s. to 100% |

* * * * *